United States Patent [19]

Bala

[11] Patent Number: 5,107,988

[45] Date of Patent: Apr. 28, 1992

[54] BITE-RESISTANT SHEATH FOR PROBE

[76] Inventor: Harry Bala, 7 Corey Dr., South Barrington, Ill. 60010

[21] Appl. No.: 507,515

[22] Filed: Apr. 11, 1990

[51] Int. Cl.⁵ .............................................. B65D 85/38
[52] U.S. Cl. .................................... 206/306; 206/212
[58] Field of Search ............... 206/212, 363, 306, 484, 206/632, 804; 229/87.01

[56] References Cited

U.S. PATENT DOCUMENTS

| | | | |
|---|---|---|---|
| 3,215,265 | 11/1965 | Welin-Berger | 206/212 |
| 3,732,975 | 5/1973 | Poncy | 206/212 |
| 3,738,172 | 6/1973 | Sato | 206/306 |
| 3,752,309 | 8/1973 | Hopkins et al. | 206/306 |
| 3,809,228 | 5/1974 | Fowler et al. | 206/306 |
| 3,847,280 | 11/1974 | Poncy | 206/212 |
| 3,850,084 | 11/1974 | Fowler et al. | 206/306 |
| 4,051,950 | 10/1977 | Jarund | 206/306 |
| 4,136,776 | 1/1979 | Poncy | 206/306 |
| 4,165,000 | 8/1979 | Poncy | 206/306 |
| 4,652,145 | 3/1987 | Bjornberg | 206/212 |
| 4,823,949 | 4/1989 | Bala | 206/306 |
| 4,846,344 | 7/1989 | Bala . | |
| 4,997,092 | 3/1991 | Dupont | 206/632 |

*Primary Examiner*—David T. Fidei
*Attorney, Agent, or Firm*—George H. Gerstman; Garrettson Ellis

[57] ABSTRACT

A sheath for a probe comprises a flattened probe sheath having an open end and a closed end. The sheath also defines a pair of peripherally connected flat sides. Each flat side of the sheath defines a distal portion and a proximal portion connected together by a transverse seal area. The proximal portion is typically made of a material which is of greater penetration strength than the distal portion. The sheath is proportioned to fit into the human mouth with the teeth normally engaging the proximal portion. Thus, the sheath is capable of substantially preventing bite-through in human mouths when enclosing a glass thermometer or other probe, while the distal end is preferably made of a softer material than each proximal portion, for an improvement in comfort.

20 Claims, 1 Drawing Sheet

BITE-RESISTANT SHEATH FOR PROBE

CROSS REFERENCE TO RELATED APPLICATION

This is a continuation in part of U.S. application Ser. No. 388,701, filed Aug. 2, 1989, now U.S. Pat. No. 5,069,337, of Harry Bala entitled Bite-Resistant Sheath for Probe.

BACKGROUND OF THE INVENTION

Sheaths for thermometers or other probes are well-known and in commercial use, being used to protect against any cross-infection from one patient to another by the reuse of incompletely sterilized thermometers or the like. Examples of such sheaths are illustrated in the pending patent applications of Harry Bala, specifically U.S. application Ser. No. 205,316, filed Jun. 10, 1988 and entitled Sheath for Probe With Improved Seal Arrangement, now U.S. Pat. No. 4,823,949; and U.S. application Ser. No. 212,969, filed Jun. 29, 1988 and entitled Sheath for Thermometer and the Like, now U.S. Pat. No. 4,846,344.

The probe sheaths of the prior art are typically made in flattened form out of a pair of flat sides, which are peripherally sealed together with the probe sheath being enclosed in a package. This of course requires the use of plastic sheeting which heat seals together in a reliable manner, such as polyethylene or poly(ethyl-methyl acrylate) also known as EMA. Additionally, poly(ethylene-vinyl acetate) (EVA) or equivalent material may be used.

The probe sheaths of the prior art perform adequately to provide a sealed sheath around oral or anal thermometers in normal circumstances. However, in the rare but unfortunate circumstances where an accident or an unruly patient breaks the thermometer during use, the probe sheaths of the prior art are sometimes of insufficient strength to avoid rupturing. This can of course cause shards of thermometer and sometimes mercury to pass into the patient. Additionally, the major purpose of the probe sheath may then fail, that is, the protection of the patient from bacterial or viral exposure from an incompletely sterilized thermometer or other probe. Particularly in the case of small children or certain disabled patients, the patients may bite through the probe sheaths of the prior art while the thermometer or other probes are inserted in the mouth, resulting in possible viral or bacterial exposure to the patient.

In accordance with this invention, an improved probe sheath is provided in which the sheath is of a strength which is capable of substantially preventing bite-through in the mouth when enclosing a glass thermometer or other probe.

While other plastic materials are known to be stronger than polyethylene, EMA, or EVA, they also tend to be stiffer. For example, biaxially oriented poly(ethylene terephthalate) or polypropylene are very strong materials, but they are relatively stiff. Thus, a flat sheath made of such strong, stiff plastic materials can be very uncomfortable in the mouth, if such flat materials penetrate a significant distance under the tongue. There, their stiff, sharp edges can press into the delicate tissues beneath the tongue and cause discomfort. Also, while such materials are heat sealable with greater difficulty and more extreme conditions than plastics such as polyethylene, they can be reliably heat sealed in manufacturing processes to provide an independent, single layer sheath portion of a strong material which cannot be bitten through under normal circumstances.

In accordance with this invention, an improved probe sheath is provided which combines strength that is sufficient to substantially prevent bite-through in the human mouth, coupled with comfort when the sheath is inserted under the tongue. With such an increase in strength, the probe sheath is also much more reliable for protection against danger from breakage of a glass thermometer or the like being used, and also increased infection against bacterial or viral exposure is provided.

DESCRIPTION OF THE INVENTION

In this invention, a sheath for a probe is provided which comprises a flat probe sheath having an open end and a closed end. The sheath defines a pair of peripherally connected, flat sides.

In accordance with this invention, each flat side of the sheath defines a distal portion and a proximal portion connected together by a transverse seal area. The proximal portion is of greater penetration strength than the distal portion, for improved bite resistance. Preferably, each distal portion is made of a softer material than each proximal portion of the flat sides of the probe sheath.

The sheath of this invention is proportioned to fit into the human mouth with such a configuration that the teeth of the mouth normally engage the proximal portion. Thus, the sheath is capable of substantially preventing bite-through in human mouths when enclosing a glass thermometer or other probe, while the distal sheath portion does not cause discomfort under the tongue.

It is often preferred for the maximum width of each distal portion to be less than the minimum width of each proximal portion. This is to say: the sheath generally tapers in width, so that the probe sheath adjacent the distal end is relatively narrow. This facilitates the comfort of the sheath under the tongue, with the probe sheath being of course, generally of the outer shape of the probe which it is intended to enclose.

Preferably, the proximal portions may be made of a stronger, and usually stiffer plastic such as polypropylene or biaxially oriented poly(ethylene terephthalate). The distal portions are preferably made of a softer material (of less penetration strength) such as polyethylene, poly(ethyl-methyl acrylate) or poly(ethylene-vinyl acetate).

It is also typical for the sheath of this invention to be enclosed between a pair of outer package sheaths, as is common in the field of probe sheaths. Likewise, in the transverse sealing area at which the distal and proximal portions are connected, the distal portions are typically positioned between the proximal portions.

Thus, a probe sheath may be provided in which the distal and proximal portions may each be of generally single-layer thickness, but the distal and proximal portions have varying physical characteristics that greatly improve the quality and utility of the probe sheath. Specifically, the proximal portion exhibits greater penetration strength to reduce the possibility of bite-through, while, preferably, the distal portion is made of a plastic material that is softer than that of the proximal portion, for greater comfort under the tongue. The probe sheath of this invention may be used for glass thermometers as stated above, or it may be used with electronic thermometer probes and the like.

DESCRIPTION OF SPECIFIC EMBODIMENTS

Figure 1:
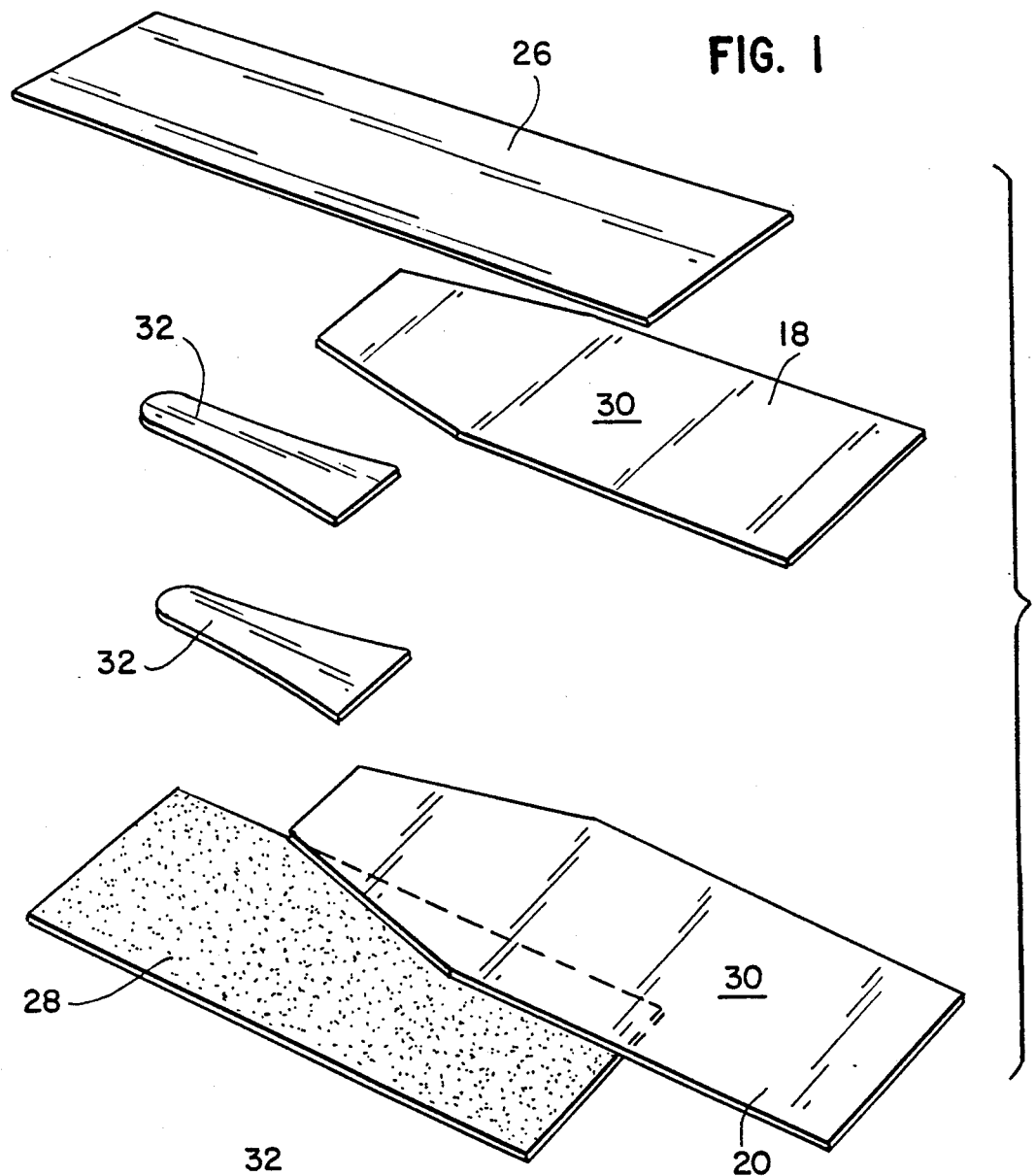
FIG. 1 is an exploded, perspective view of individual parts of the probe sheath of this invention.

Referring to the drawings, a probe sheath 10 is shown, being specifically of the design to receive an electronic thermometer probe, for protection of the patient against the transfer of disease organisms as the probe is inserted into the mouth.

Figure 2:
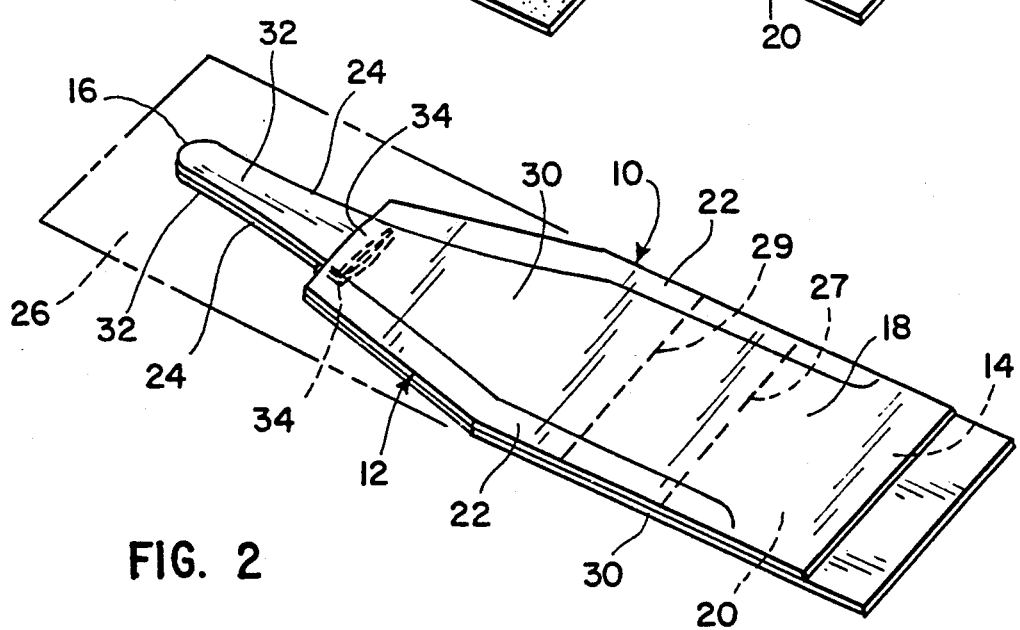
FIG. 2 is a perspective view of the assembled probe sheath made of the parts of FIG. 1, with the outer package sheets of the assembled probe sheath package being shown in phantom lines.

As shown particularly in FIG. 2, sheath 10 comprises a flattened probe sheath 12 which has an open end 14 through which a probe may be inserted, and a closed end 16. Sheath 12 defines a pair of flat sides 18, 20, which are sealed together along peripheral seals 22, 24 by any conventional manner, typically by means of a heat seal process.

As is conventional, probe sheath 12 is usually enclosed between a pair of outer package sheath 26, 28, which may also be peripherally sealed together.

Many different designs of sheaths for a probe, made of layers of peripherally sealed plastic sheets, are well known, and the invention of this application may be incorporated in conjunction with many of those different designs. However, in the specific embodiments shown, probe sheath 12 is not sealed to the envelope defined by the package sheets 26, 28, so that probe sheath 12 may be grasped near its open end 14 and pulled out of engagement with the envelope defined by the package sheets 26, 28. In other embodiments, the respective sheets of probe sheath 12 and the package sheets 26, 28 may be sealed together, with the package being opened in a variety of different, known ways.

In accordance with this invention, each of the flat sides 18, 20 define a proximal portion 30 and a distal portion 32. As shown in FIG. 2, each proximal portion 30 of a side is connected to the corresponding distal portion 32 of the same side by a transverse seal line 34, which may be a heat seal line, so that a unitary sheath may be provided having an openable interior between the respective proximal portions 30 and distal portions 32, while being laterally sealed by seal lines 22, 24, and the respective proximal and distal portions are sealed together at transverse seal lines 34, each of which may be a conventional heat seal. Alternatively, adhesive may be provided at transverse seal 34 line or elsewhere if desired.

Proximal portions 30 may be made of a plastic material such as polypropylene or poly(ethylene terephthalate) typically of the biaxially oriented form, to be of greater penetration strength than the distal portions 32. Furthermore, sheath 12 is proportioned so that proximal portions 30 are longer than distal portions 32, to provide a fit into the human mouth so that the teeth, when closed, normally engage proximal portions 30, when sheath 12 is normally positioned under the tongue. Such a sheath may be capable of substantially preventing bite-through in the human mouth when enclosing a glass thermometer or other probe such as an electronic thermometer probe. The thickness of proximal plastic layers 30 is typically from 0.005 to 0.002 inch, so that good bite-resistance and strength is provided at low cost when a material such as Mylar brand polyester film is used.

The material of distal portions 32, on the other hand, is generally substantially softer than the material of proximal section 30, and consequently tends to be of less penetration strength than proximal portions 30. Such softer materials provide better comfort under the tongue, for example, than do the stronger materials of proximal portion 30, so that the users of the probe sheath do not feel discomfort in the area where the probe is deeply embedded under the tongue. At the same time, good bite-resistance is provided to the sheath at the position where biting is likely to take place.

Typically, distal portions 32 may be made of a softer plastic such a polyethylene, poly(ethyl-methyl acrylate) or poly(ethylene vinyl acetate), which materials are readily heat sealable along transverse seal line 34 to the proximal sections 30, and are readily heat sealable to each other along peripheral seal line 24. Typically, the thickness of each distal plastic layer 32 is about 0.001 to 0.002 inch to provide adequate strength under the potentially less severe conditions that inner plastic layers 32 are expected to encounter, coupled with good heat transfer capability, so that the thermometer may rapidly sense the temperature of the patient.

It is generally preferred for the sheath of this invention to define a wall about its thermometer or other probe which is only a single layer thick, except for the transverse seal area 34, where a double thickness is found. This single layer is of course defined by the distal portions 32 of the flat sides distal to transverse seal 34, and the proximal portions 30 of the flat sides proximal to the seal line 34. Thus, the probe sheath of this invention uses only a small amount of material, and is easily manufactured at low cost. Nevertheless, the probe sheath combines high strength and especially good bite-resistance where it is expected to be needed, coupled with a softer, distal sheath portion for improved comfort under the tongue when a thermometer or other probe is within the sheath.

A thermometer or other probe may be inserted in conventional manner by pulling apart the proximal sheath portions at open end 14 and inserting the thermometer. This may take place either before or after removal of the outer package sheaths 26, 28. The sheath may be used in the conventional manner of commercially available sheaths, but with the advantages provided by this invention as previously described.

The above has been offered for illustrative purposes only, and is not intended to limit the scope of the invention of this application, which is as defined by the claims below.

That which is claimed is:

1. In a sheath for a probe which comprises a flattened probe sheath having an open end and a closed end, said probe sheath defining a pair of peripherally connected, flat sides, the improvement comprising, in combination:

each flat side of said probe sheath defining a distal portion and a proximal portion connected together by a transverse seal area, said proximal portion being of greater length and penetration strength than said distal portion, said probe sheath being proportioned to fit into the human mouth with the teeth normally engaging said proximal portion whereby said sheath is capable of substantially preventing bite-through in human mouths when enclosing a glass thermometer or other probe.

2. The probe sheath of claim 1 in which each distal portion is made of a softer material than each proximal portion.

3. The probe sheath of claim 1 in which the maximum width of each distal portion is less than the minimum width of each proximal portion.

4. The probe sheath of claim 1 in which said proximal portions are made of polypropylene or biaxially oriented poly(ethylene terephthalate).

5. The probe sheath of claim 1 in which said distal portions are made of polyethylene, poly(ethyl-methyl acrylate), or poly(ethylene-vinyl acetate).

6. The probe sheath of claim 1 in which said probe sheath is enclosed between a pair of outer package sheets.

7. The probe sheath of claim 1 in which, in the transverse seal area, said distal portions are positioned between said proximal portions.

8. The probe sheath of claim 1 in which said distal and proximal portions are each of single-layer thickness.

9. In a sheath for a probe which comprises a flattened probe sheath having an open end and a closed end, said probe sheath defining a pair of peripherally connected, flat sides, the improvement comprising, in combination:

each flat side of said probe sheath defining a distal portion and a proximal portion connected together by a transverse seal area, said proximal portion being made of polypropylene or poly(ethylene terephthalate), and said distal portion being made of polyethylene, poly(ethyl-methyl acrylate), or poly(ethylenevinyl acetate), and said proximal portion has greater length and penetration strength than said distal portion.

10. The probe sheath of claim 9 which is proportioned to fit into the human mouth with the teeth normally engaging said proximal portion, to be capable of substantially preventing bite-through in the human mouth when enclosing a glass thermometer or other probe.

11. The probe sheath of claim 10 in which the maximum width of each distal portion is less than the maximum width of each proximal portion.

12. The probe sheath of claim 10 in which said probe sheath is enclosed between a pair of outer package sheets.

13. The probe sheath of claim 12 in which said distal and proximal portions are each of single-layer thickness.

14. The probe sheath of claim 13 in which, in the transverse seal area, said distal portions are positioned between said proximal portions.

15. The probe sheath of claim 10 in which each distal portion is made of a softer material than each proximal portion.

16. In a sheath for a probe which comprises a flattened probe sheath having an open end and a closed end, said probe sheath defining a pair of peripherally connected, flat sides, the improvement comprising, in combination:

each flat side of said probe sheath defining a distal portion and a proximal portion connected together by a transverse seal area, said proximal portion having a greater penetration strength than said distal portion, said proximal portion being made of a different and stronger plastic material than said distal portion, the proximal and distal portions of said probe sheath being proportioned to fit into the human mouth so that the teeth normally engage said proximal portion, whereby said probe sheath is capable of substantially preventing bite-through in human mouths while enclosing a glass thermometer or other probe, while said distal portion is normally spaced from the teeth in a human mouth; said distal portion being made of softer material than said proximal portion.

17. The probe sheath of claim 16 in which the majority of the length of said probe sheath comprises single layer segments, the majority of each distal portion being longitudinally spaced from the proximal portions and the majority of each proximal portion being longitudinally spaced from each distal portion.

18. The probe sheath of claim 17 in which, in said transverse seal area, said distal portions are positioned between said proximal portions.

19. The probe sheath of claim 18 in which the maximum width of each distal portion is less than the minimum width of each proximal portion.

20. The probe sheath of claim 19 in which said probe sheath is enclosed between a pair of outer package sheaths.

* * * * *